United States Patent [19]

Diettrich, Jr. et al.

[11] Patent Number: 4,556,489
[45] Date of Patent: Dec. 3, 1985

[54] MEMBRANE OXYGENATOR

[75] Inventors: Lambert J. Diettrich, Jr., Leucadia; Francis M. Servas, San Juan Capistrano, both of Calif.

[73] Assignee: Shiley Incorporated, Irvine, Calif.

[21] Appl. No.: 473,508

[22] Filed: Mar. 9, 1983

[51] Int. Cl.$^4$ .................................................. B01D 31/00
[52] U.S. Cl. ............................ 210/321.3; 210/493.5; 422/48
[58] Field of Search ............... 210/493.5, 321.3, 321.4, 210/321.5, 321.2, 321.1; 422/48

[56] References Cited

U.S. PATENT DOCUMENTS

| 3,060,934 | 10/1962 | Claff et al. | 128/214 |
|---|---|---|---|
| 3,342,719 | 9/1967 | Chen et al. | 204/301 |
| 3,370,710 | 2/1968 | Bluemle, Jr. | 210/321 |
| 3,396,849 | 8/1968 | Lande et al. | 210/321 |
| 3,459,310 | 8/1969 | Edwards | 210/321 |
| 3,522,885 | 8/1970 | Lavender et al. | 210/321 |
| 3,534,860 | 10/1970 | Dibelius et al. | 210/321 |
| 3,541,595 | 11/1970 | Edwards | 210/321 |
| 3,560,340 | 2/1971 | Leonard | 195/1.8 |
| 3,565,258 | 2/1971 | Lavender | 210/321 |
| 3,585,131 | 6/1971 | Esmond | 210/321 |
| 3,612,281 | 10/1971 | Leonard | 210/321 |
| 3,684,097 | 8/1972 | Mathewson, Jr. et al. | 210/321 |
| 3,695,445 | 10/1972 | Esmond | 210/321 |
| 3,729,098 | 4/1973 | Serur | 210/321 |
| 3,730,350 | 5/1973 | Hoeltzenbein | 210/321 |
| 3,738,495 | 6/1973 | Esmond | 210/321 |
| 3,757,955 | 9/1973 | Leonard | 210/321 |
| 3,780,870 | 12/1973 | Esmond | 210/321 |
| 3,788,482 | 1/1974 | Markley | 210/321 |
| 3,839,204 | 10/1974 | Ingenito et al. | 210/181 |
| 3,862,031 | 1/1975 | Leonard | 210/321 |
| 3,864,265 | 2/1975 | Markley | 210/321 |
| 3,879,293 | 4/1975 | Wolf, Jr. et al. | 210/321 |
| 3,907,687 | 9/1975 | Hoeltzenbein | 210/321 |
| 4,016,081 | 4/1977 | Martinez et al. | 210/321 B |
| 4,022,692 | 5/1977 | Janneck | 210/321 B |
| 4,028,252 | 6/1977 | Morris | 210/321 B |
| 4,054,527 | 10/1977 | Esmond | 210/321 B |
| 4,116,841 | 9/1978 | Borsanyi | 210/321 B |
| 4,199,457 | 4/1980 | Esmond | 210/321 B |
| 4,213,858 | 7/1980 | Boberg et al. | 210/23 R |
| 4,219,422 | 8/1980 | Knothe et al. | 210/137 |
| 4,246,121 | 1/1981 | Corbin, III et al. | 210/493.5 X |
| 4,304,669 | 12/1981 | Knothe et al. | 210/321.2 |
| 4,351,797 | 9/1982 | Bellhouse et al. | 422/48 |
| 4,374,802 | 2/1983 | Fukasawa | 422/48 |
| 4,404,100 | 9/1983 | Mikhail | 210/232 |

FOREIGN PATENT DOCUMENTS

1433512 4/1976 United Kingdom ............ 210/321.3

Primary Examiner—Frank Spear
Attorney, Agent, or Firm—Charles J. Knuth; Peter C. Richardson; Lawrence C. Akers

[57] ABSTRACT

A novel device for mass transfer across a membrane is disclosed, which is particularly suitable for use as a blood oxygenator. The novel device is of the type having a pleated, selectively permeable membrane defining first and second sets of alternating pockets for the flow of a fluid to be treated (e.g. blood) and a treating fluid (e.g. oxygen), and a discrete support screen disposed within each of the pockets of said first and second sets. Of considerable importance is the feature that the support screens are designed to be substantially interdigitated when the assembly of membrane and support screens is held as a compressed stack within the housing of the device. The novel mass transfer apparatus may be utilized as a compact blood oxygenator with excellent gas transfer rates, low pressure drops and negligible trauma to blood components.

12 Claims, 14 Drawing Figures

MEMBRANE OXYGENATOR

BACKGROUND OF THE INVENTION

During surgical procedures such as cardiopulmonary bypass operations it is possible to replace the function of the lungs with an extracorporeal blood oxygenator. Venous blood is passed in an extracorporeal circuit through the oxygenator, arterialized (i.e. oxygenated) and returned to the patient's body. One well known type of blood oxygenator is the bubble oxygenator in which treating gas (e.g. oxygen) bubbles are created and brought into direct contact with the venous blood stream, with resulting mass transfer of oxygen from the bubbles to the blood and of carbon dioxide from the blood to the bubbles. Although bubble blood oxygenators have been employed for many years with considerable success, their use is characterized by an inherent disadvantage, which is the need to create a blood foam to accomplish gas transfer. The bursting of gas bubbles into the blood stream during the creation of the foam may give rise to deleterious hemolysis. Furthermore, the blood foam must be thoroughly treated after oxygenation, typically in a defoamer and an arterial filter, to remove gaseous bubbles and emboli before the arterialized blood can be returned to the patient.

Another well known type of blood oxygenator, the membrane oxygenator, does not require formation of a blood foam to accomplish gas transfer. Blood and treating gas streams flow in the oxygenator separated by a semipermeable membrane, through which oxygen passes to the blood, carbon dioxide passes from the blood, while water and other non-gaseous blood components do not pass. In designing a membrane oxygenator for use in typical extracorporeal circuits, it is a desired goal to provide adequate gas transfer capacity to process the anticipated blood flows (from about 2 liters/min. to about 6 liters/min.) while maintaining a compact size for convenient handling, priming and operation, avoiding excessive blood and treating gas pressure drops and preventing significant trauma to blood components.

Blood membrane oxygenators of the general type having a pleated, semipermeable membrane held in a housing with support screens positioned in alternating blood and oxygen passageways are known (see, for example, U.S. Pat. Nos. 3,560,340; 3,612,281; 3,780,870 and 4,199,457). However, none of the membrane oxygenators disclosed in said U.S patents fully satisfy all of the criteria set forth above in the preceding paragraph. U.S. Pat. No. 4,028,252 discloses a blood dialyzer containing a single sheet of membrane and a single length of non-woven support material accordion-folded together to form alternating blood and dialysate flow paths separated by the membrane, with the support material being capable of interdigitation when folded upon itself. Accordingly, the support material is located on only one side of the membrane in this prior art dialyzer. U.S. Pat. No. 213,858 discloses the use of three-layer non-woven "supporting nets" in blood dialyzers and oxygenators, adjacent units of which are capable of interdigitation. However, even when such interdigitation occurs, the flow passageway defined by two portions of membrane separated by one of the supporting nets is at least about as thick as the middle layer of the supporting net and thus occupies more volume than desired in an extracorporeal blood oxygenator.

SUMMARY OF THE INVENTION

The present invention comprises a mass transfer device for the treatment of blood, e.g. a blood oxygenator or blood dialyzer, comprising a housing; a pleated, selectively permeable membrane disposed within the housing in substantially rectangular folds defining first and second sets of alternating pockets for the flow of blood and a treating fluid; a plurality of discrete non-woven support screens having substantially the same width as said folds, with one of said screens being disposed within each of said pockets of said first and second sets, said membrane and screens being held in said housing as a compacted stack compressed in a direction normal to the substantially rectangular surfaces of said folds with the screens disposed within adjacent blood and treating fluid pockets and separated by the membrane being substantially interdigitated, and with said support screens consisting essentially of a first layer in a first plane of first strands spaced apart and substantially parallel to one another and a second layer in a second plane of second strands spaced apart and substantially parallel to one another, said first layer and said second layer being bonded together at points of contact and said first strands being oriented with respect to said second strands at an angle of from about 45° to 90°; blood inlet and outlet means in the housing adjacent opposed ends of said stack in communication with the first set of pockets, thereby establishing overall blood flow paths in the first set of pockets along the length of said pockets; and treating fluid inlet and outlet means in the housing adjacent opposed ends of said stack in communication with the second set of pockets, thereby establishing overall treating fluid flow paths in the second set of pockets along the length of said pockets.

When the treating fluid is an oxygen-containing gas, the novel mass transfer device is a highly efficient membrane blood oxygenator. The interdigitation of adjacent support screens allows for the compression of the stack of pleated membrane and screens into a small prism-shaped volume, without reducing the membrane surface area available for mass transfer. As a result of its low volume, the oxygenator is easy to handle and operate and requires only a minimal amount of blood or other liquid for priming. High oxygen and carbon dioxide transfer rates between the blood and treating gas are attainable. The interdigitation of pairs of adjacent screens, with a membrane fold trapped between each pair, creates thin, highly convoluted local flow paths in the blood and gas pockets, thereby causing a high degree of beneficial fluid mixing and crossflow of blood and treating gas in said pockets. Because diffusion through the blood streams will usually be the rate-determining step for gas transfer in the oxygenator, improved mixing characteristics in the blood flow pockets are particularly significant. Treating gas and blood pressure drops across the oxygenator are quite acceptable and trauma to blood components is minimal. Preferably, in order to maximize the advantageous fluid flow characteristics in the blood and treating gas pockets, the first strands and the second strands in the blood pocket and treating gas pocket support screens are all oriented at acute angles of from about 20° to about 70° with respect to the fold lines of the membrane.

The mass transfer rates in a device of the invention can be further improved without excessively increasing the blood pressure drop across the device by providing appropriate shims between the two opposed side walls of the oxygenator housing and the compacted stack of membrane and screens. Each of these two shims is centrally disposed between the ends of the stack, is at least about as wide as the stack, has a length of from about 10% to about 50% of that of the stack and has a thickness of from about 1% to about 10% of the height of the compacted stack. Additionally, blood and treating fluid pressure drops across a mass transfer device of the type disclosed herein can be reduced and fluid distribution over the width of the pockets improved by providing appropriate transversely-extending cut-out regions in the corresponding support screens adjacent the opposed ends thereof.

DETAILED DESCRIPTION OF THE INVENTION

The invention will be described in detail with reference to a preferred embodiment thereof, which is an extracorporeal membrane blood oxygenator in assembly with an integral heat exchanger. Reference to this embodiment does not limit the scope of the invention, which is limited only by the scope of the claims. In the drawings:

Figure 1:
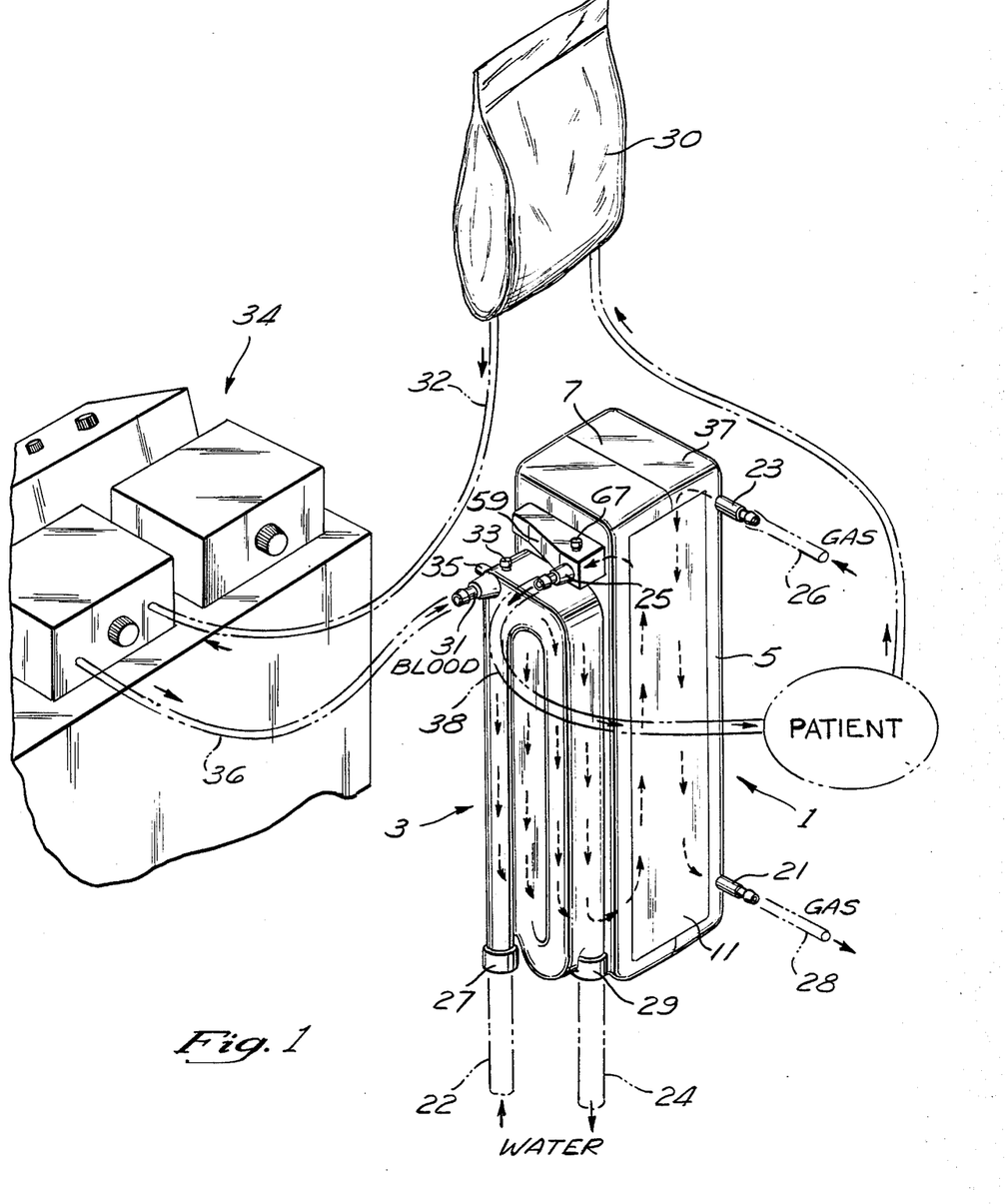
FIG. 1 is a perspective view of an assembly of a membrane blood oxygenator of the invention and an integral heat exchanger, shown schematically in position in a typical extracorporeal blood circuit.
Figure 2:
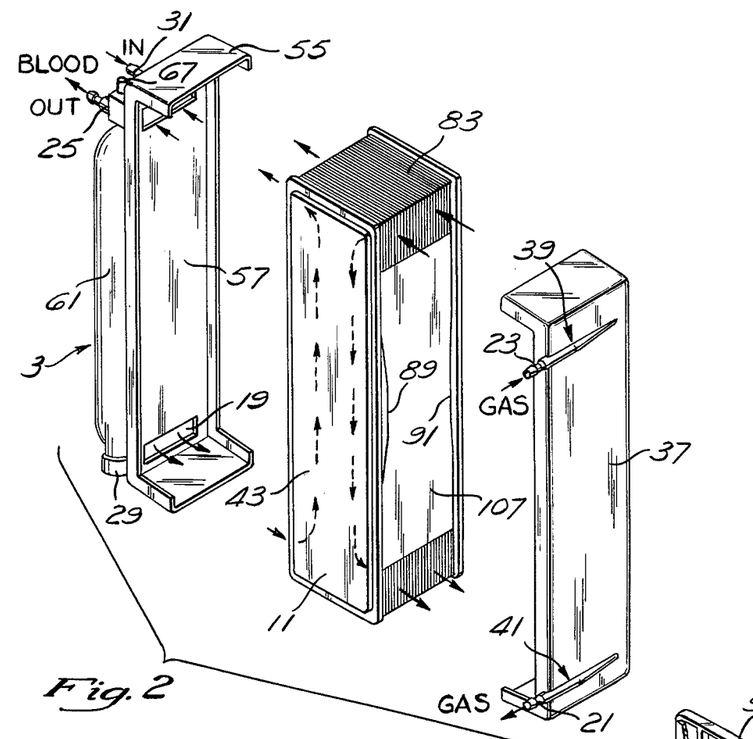
FIGS. 2 and 3 are exploded perspective views of the assembly of FIG. 1.
Figure 3:
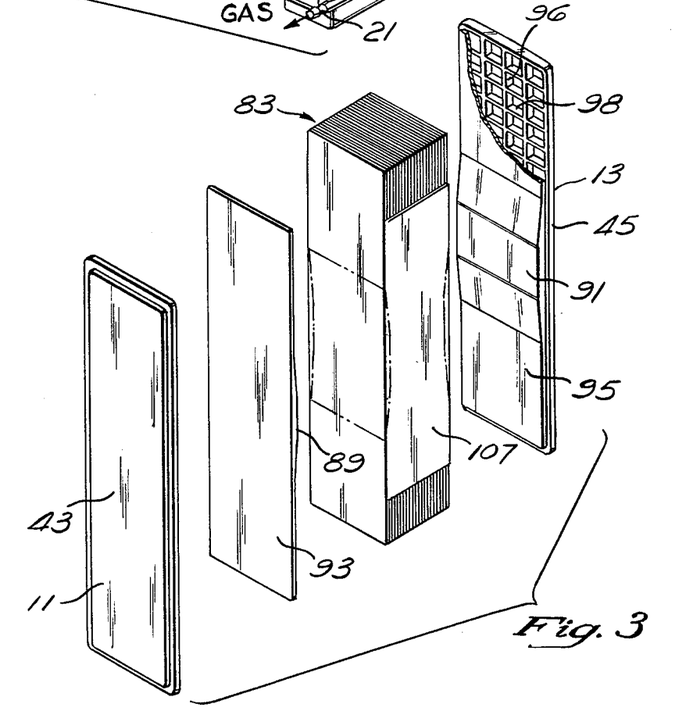
Figure 4:
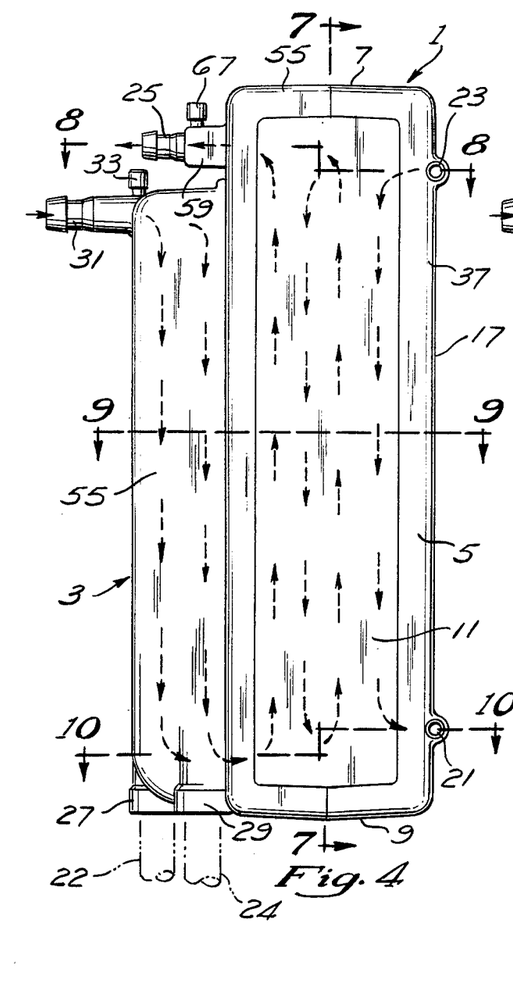
FIG. 4 is a side plan view of the assembly of FIG. 1.
Figure 5:
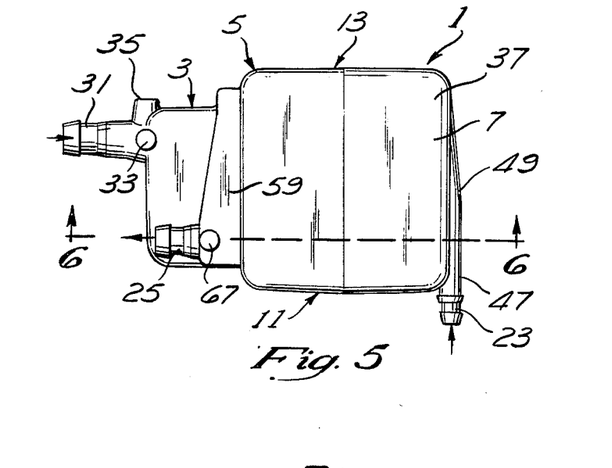
FIG. 5 is a top plan view of the assembly of FIG. 1.
Figure 6:
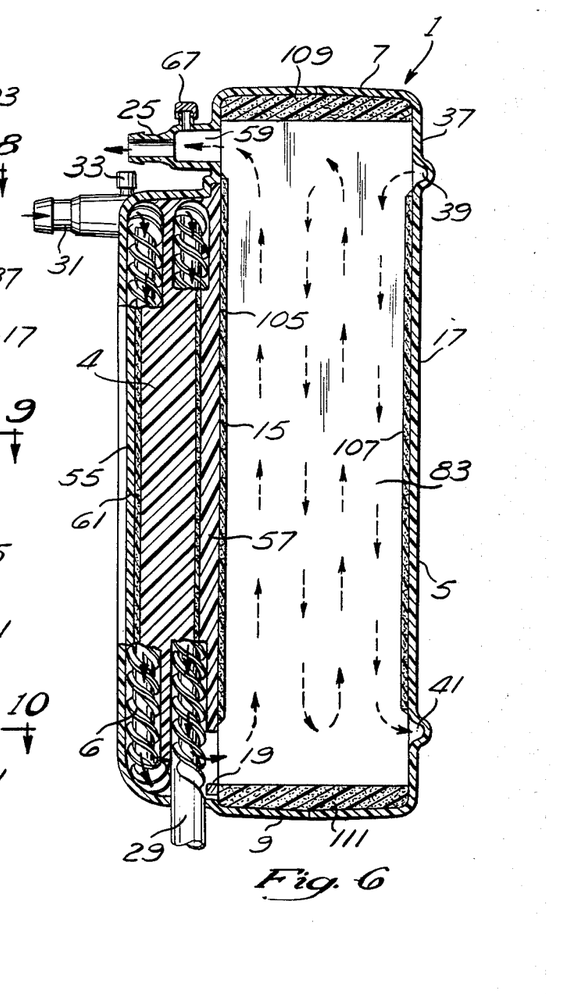
FIG. 6 is a section view, taken along line 6—6 in FIG. 5.

A disposable assembly of a blood membrane oxygenator 1 of the invention and an integral heat exchanger 3 is shown in FIGS. 1 to 10. This assembly is adapted to be incorporated in an extracorporeal blood circuit in the vertically-extending orientation shown in FIG. 1. Oxygenator 1 comprises a housing 5 in the general shape of a rectangular prism, a blood inlet 19 and a treating gas outlet 21 adjacent the bottom end of the housing, and a treating gas inlet 23 and a blood outlet 25 adjacent the top end of the housing. Housing 5 includes a top wall 7, a bottom wall 9, opposed side walls 11 and 13, a front wall 15 and a rear wall 17. Integral heat exchanger 3, which does not constitute a part of the present invention, treats the venous blood upstream of the oxygenator 1 and is provided with a cooling water inlet 27 and a cooling water outlet 29, both of which include a quick-disconnect fitting, and a heat exchanger blood inlet 31. As shown in FIG. 1, a sample port 33 and a temperature probe 35 may be provided in or near the heat exchanger blood inlet 31. Heat exchanger 3 includes a single cooling fluid-conducting tube 6 provided with a continuous hollow helical rib forming a helical flute and a plastic coil-supporting core piece 4. The venous blood, which divides and flows downwardly through heat exchanger 3 along the four turas of coil 6 (note arrows in FIG. 1), is constrained by the surfaces of coil 6, core piece 4, blood manifold plate 55 and retainer plate 57 to follow locally the track defined by the helical flute. As a result, an extended contact time between the venous blood and coil 6 can be realized.

Rear wall 17 and approximately one-half of each of top wall 7 and bottom wall 9 of housing 5 are formed by a gas manifold plate 37, which plate includes in single piece construction therewith treating gas inlet 23, a treating gas inlet manifold 39, treating gas outlet 21 and a treating gas outlet manifold 41. Each of manifolds 39 and 41 contains a constant cross-sectional diameter portion 47, 51 adjacent the treating gas inlet or outlet and a tapered portion 49, 53 removed from said inlet or outlet. This manifold configuration serves to prevent formation of zones of fluid stagnation within the manifolds. Side walls 11 and 13 of housing 5 are formed, respectively, by pressure plates 43 and 45. Approximately one-half of each of top wall 7 and bottom wall 9 and a portion of front wall 15 of housing 5 are formed by a blood manifold plate 55. The remainder of front wall 15 is formed by a retainer plate 57 (see FIGS. 6 and 9). Plate 55 includes in single piece construction therewith blood outlet 25, a blood outlet manifold 59, heat exchanger blood inlet 31 and a heat exchanger housing wall 61. The cooling water coils of heat exchanger 3 are held between plate 57 and wall 61. In order to prevent formation of zones of fluid stagnation therein, manifold 59 is tapered with decreasing cross-sectional diameter away from blood outlet 25. As shown in FIG. 1, a sample port 67 may be provided in blood outlet 25 and a temperature probe 69 in manifold 59. The blood inlet of oxygenator 1 (and also the blood outlet of heat exchanger 3) is a substantially rectangular slot 19 in retainer plate 57.

Oxygenator 1 also includes a pleated, selectively permeable membrane 71 disposed within housing 5 in rectangular folds parallel to walls 11 and 13. These folds define first and second sets 73 and 75 of alternating pockets for the flow of blood and a treating gas, respectively. The fold lines of pleated membrane 71 are situated adjacent walls 15 and 17 of housing 5. Blood inlet 19 and blood outlet 25 are in fluid communication with the first set 73 of pockets, while treating gas inlet 23 and treating gas outlet 21 are in fluid communication with the second set 75 of pockets. Thus, overall countercurrent blood and treating gas flow paths are established in sets 73 and 75, respectively, of pockets along the length of said pockets. In a membrane blood oxygenator such as oxygenator 1, the membrane should be permeable to oxygen and carbon dioxide, but impermeable to water and other non-gaseous blood constituents. Any of the known types of membrane materials conventionally employed in blood membrane oxygenators may be utilized in a blood oxygenator of the present invention. As only one example, membrane 71 of oxygenator 1 may be made of a microporous polypropylene membrane material sold by Celanese Corp. (New York, N.Y.) under the trade name Celgard.

A very important feature in the design of oxygenator 1 is the presence, in each of the pockets of sets 73 and 75, of a discrete non-woven support screen, e.g. 77, 79 and 81, having substantially the same width as the rectangular folds of membrane 71. Preferably, in order to improve the distribution of fluids into the various pockets in the two sets 73 and 75 and to reduce pressure drops, these support screens are made to be slightly wider (by from about 0.02 in. to about 0.03 in.) than the membrane folds. As a result, the screens will be exposed in the vicinity of inlet 19 and manifolds 39, 41 and 59. Also, the support screens preferably have substantially the same length as said rectangular folds. In oxygenator 1, membrane 71 and its associated support screens are held in housing 5 as a compacted stack 83 compressed by side walls 11 and 13 in a direction normal to the rectangular surfaces of the support screens and membrane folds (see FIGS. 8 to 10). The opposed ends of stack 83 are situated adjacent walls 7 and 9, while the top and bottom of stack 83 are situated adjacent walls 11 and 13, respectively. Three of the support screens utilized in oxygenator 1 are shown in detail in FIG. 14, with two adjacent folds of membrane 71 held between them. It is to be understood that the actual stack of membrane folds and support screens in oxygenator 1 extends above and below the partial assembly depicted in FIG. 14. Each of the support screens in stack 83, e.g. screen 77, consists of a first layer, e.g. 85, of straight strands in a first plane spaced apart and parallel to one another and a second layer, e.g. 87, of straight strands in a second plane spaced apart and parallel to one another. The strands of said first layer are bonded to the strands of said second layer at their points of mutual contact, e.g. by adhesive or fusion bonding, and the strands of the first layer are oriented with respect to the strands of the second layer at an angle A of from about 45° to 90°. Angle A is substantially the same in every screen in stack 83. Preferably, the strands of the support screens in stack 83 are of cylindrical crosssection, with the strands in both layers of the screens in the set of blood pockets 73 having the same crosssectional diameter $d_1$ and the strands in both layers of the screens in the set of treating gas pockets 75 have the same cross-sectional diameter $d_2$, and $d_1$ and $d_2$ each being of from about 0.008 in. to about 0.016 in. Most preferably, $d_1$ is equal to $d_2$. In both the blood pocket and treating gas pocket support screens, the individual parallel strands in each of the two layers are preferably separated by from about 0.05 in. to about 0.10 in. As one example, the support screens in stack 83 may be cut from the same sheet of an open mesh polymeric material such as the extruded medical grade non-woven open mesh polypropylene screen material sold by NSW & Co. (Roanoke, Va.) under the tradename Polynetting, with the cutting lines in said sheet of the longitudinal edges of the blood screens all being substantially parallel, the cutting lines in said sheet of the longitudinal edges of the treating gas screens all being substantially parallel, and the cutting direction of the blood screen longitudinal edges being substantially perpendicular in said sheet to the cutting direction of the treating gas screen longitudinal edges. Alternatively, the two sets of support screens may be cut from different non-woven stock materials, with the strand pattern in the stock material from which the blood pocket support screens are cut being a mirror image of the strand pattern in the stock material from which the treating gas pocket support screens are cut.

Figure 14:
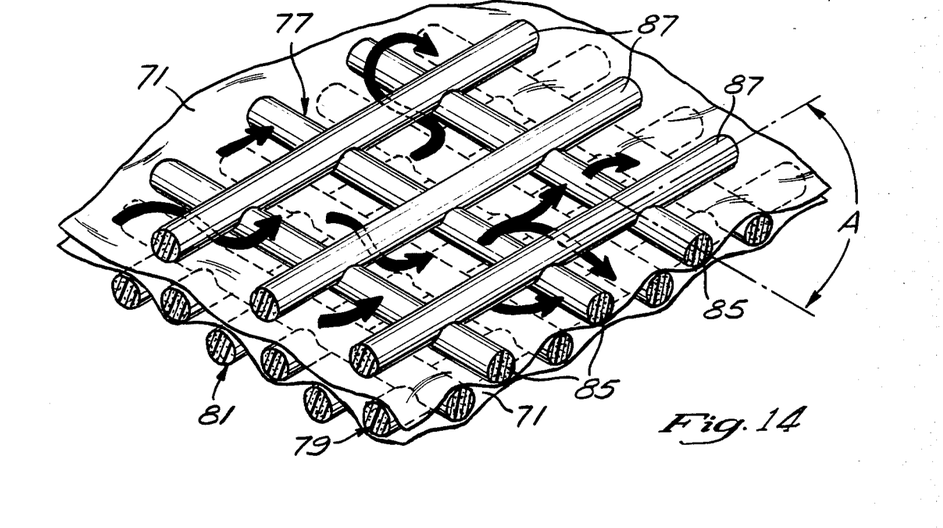
FIG. 14 is a perspective view of three adjacent support screens in the compressed stack shown in FIG. 11 and the two adjacent membrane folds held between said screens, with schematic representation of the local blood flow paths through one of the blood pockets in the oxygenator of FIG. 1.

When assembled in stack 83 with the folds of membrane 71, adjacent support screens line up in the manner shown in FIG. 14, i.e. with the strands of each layer in each screen, e.g. screen 79, substantially parallel to the strands of the adjacent layer in the next screen in the stack, e.g. screens 77 and 81. As a result of this orientation, the support screens disposed within adjacent blood and treating gas pockets in oxygenator 1 become substantially interdigitated when the assembly of membrane and screens is compressed (e.g. by pressure plates 43 and 45) in a direction normal to the rectangular surfaces of the folds of the membrane. As used herein, the term "substantially interdigitated" means that two adjacent support screens are interdigitated over at least 50 percent of their common interfacing gross surface area.

The substantial interdigitation of adjacent support screens in oxygenator 1 has several important benefits. First of all, for a particular membrane surface area available for mass transfer, the volume of stack 83 and thus of oxygenator 1 is greatly reduced. As a result, the manufacturing, shipping, handling, setting up, priming, operation and disposal of the oxygenator are facilitated. Additionally, the interdigitated support screens create networks of thin, highly convoluted flow paths in the blood and treating gas pockets (see, for example, the multitude of interconnected blood flow paths depicted by arrows in FIG. 14 in the pocket containing support screen 77). As the blood and treating gas pass along their thin convoluted flow paths, a high degree of intraphase fluid mixing occurs within the various flow pockets along with a high degree of crossflow of the blood and treating gas in adjacent pockets. The net result is a highly efficient mass transfer of oxygen to, and carbon dioxide from, the blood with minimal trauma to blood constituents (e.g. minimal hemolysis) and acceptable blood and treating gas pressure drops across the oxygenator. Preferably, the support screens are cut so that the strands in both layers of the blood pocket and treating gas pocket support screens are all oriented at acute angles of from about 20° to about 70° with respect to the fold lines of membrane 71. Since the overall flow paths of blood and treating gas are parallel to these fold lines, the strands oriented in such a manner act as a very highly effective series of flow distributors, thereby further enhancing the advantageous flow characteristics in the blood and treating gas pockets and essentially eliminating any tendency for channeling to occur. More preferably, the strands in both layers of the blood pocket support screens are oriented at substantially the same acute angle with respect to the fold lines of membrane 71 and the same is true for the strands in both layers of the treating gas pocket support screens (note angles $B_1$ and $B_2$ in FIG. 11). Since extensive flow distribution of blood is more important than that of treating gas, angle $B_1$ (blood screens) is most preferably greater than angle $B_2$ (treating gas screens).

Figure 11:
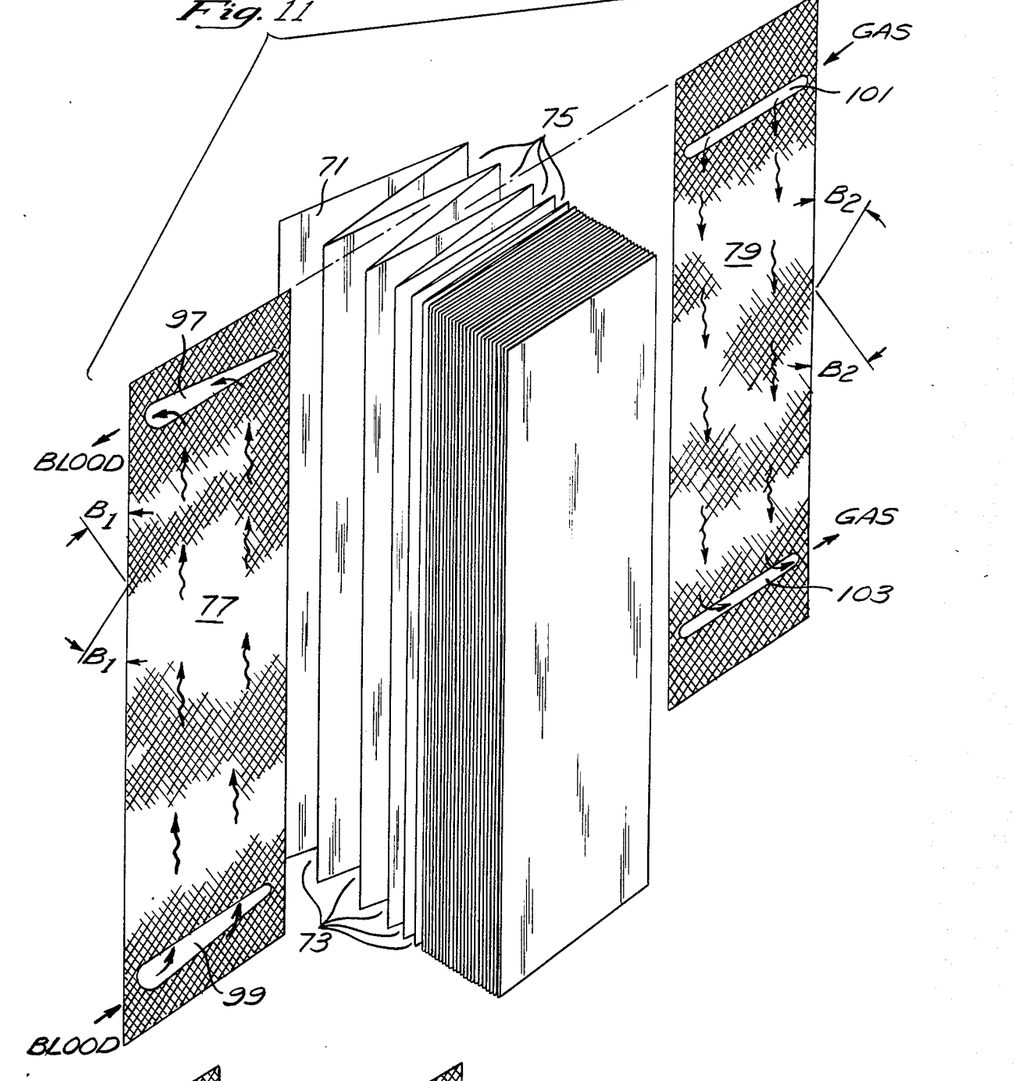
FIG. 11 is a view, partially in exploded form, of the stack of pleated membrane and support screens in the oxygenator of FIG. 1.
Figures 12, 13:
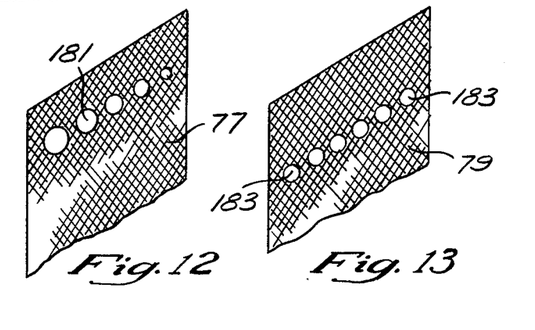
FIGS. 12 and 13 show alternative designs for the transversely-extending cut-out regions in the support screens in the oxygenator of FIG. 1.

Another highly advantageous feature of oxygenator 1 is depicted in FIG. 11. Each of the support screens in the stack 83 is provided with a pair of transversely-extending slots, e.g. slots 97 and 99 in screen 77 and slots 101 and 103 in screen 79, one adjacent each opposed end of the screen. The slots in the blood pocket support screens in stack 83 are located directly below blood inlet 19 and blood outlet manifold 59, while the slots in the treating gas pocket support screens in stack 83 are located directly above treating gas inlet manifold 39 and treating gas outlet manifold 41. The slots in the support screens disposed in set 73 of blood pockets are tapered with decreasing width away from blood inlet 19 and blood outlet manifold 59 and may, as shown in FIG. 11, be substantially trapezoidal. The slots in the support screens in set 75 of treating gas pockets may also be tapered with decreasing width away from rear wall 17 but are not necessarily so tapered and may, as shown in FIG. 11, be substantially rectangular. Alternatively, any other type of transversely-extending cut-out regions may be formed in the various support screens, such as the series of circular holes, e.g. 181, with decreasing diameter shown in FIG. 12 for blood pocket screens and the series of circular holes, e.g. 183, with constant diameter shown in FIG. 13 for treating gas pocket screens. The cut-out regions in the support screens may be formed with a steel rule die simultaneously with the cutting of the screens from a sheet of open mesh stock material. The purpose of the transverse cut-outs in the blood pocket and treating gas pocket support screens is to enhance the distribution of blood and treating gas across the width of said pockets. Such enhanced fluid distribution results in a full efficient utilization of membrane surface area for mass transfer and in reduced blood and treating gas pressure drops across the oxygenator. Although this aspect of the invention is preferably practiced with the non-woven, interdigitated support screens of oxygenator 1, it is to be understood that its contemplated scope of applicability is not so limited. Thus, transversely-extending fluid distribution cut-out regions according to this aspect of the invention might be provided in, for example, woven and/or non-interdigtated support screens disposed within the alternating blood and treating gas pockets defined by a pleated, selectively-permeable membrane of any blood membrane oxygenator of this general class.

Figure 7:
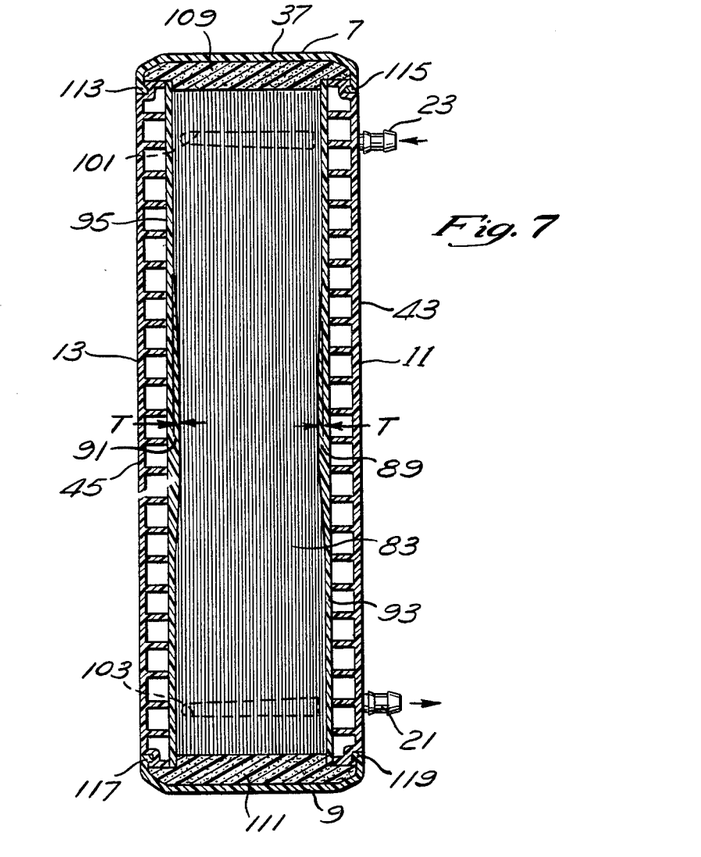
FIG. 7 is a section view, taken along line 7—7 in FIG. 4.
Figures 8, 9:
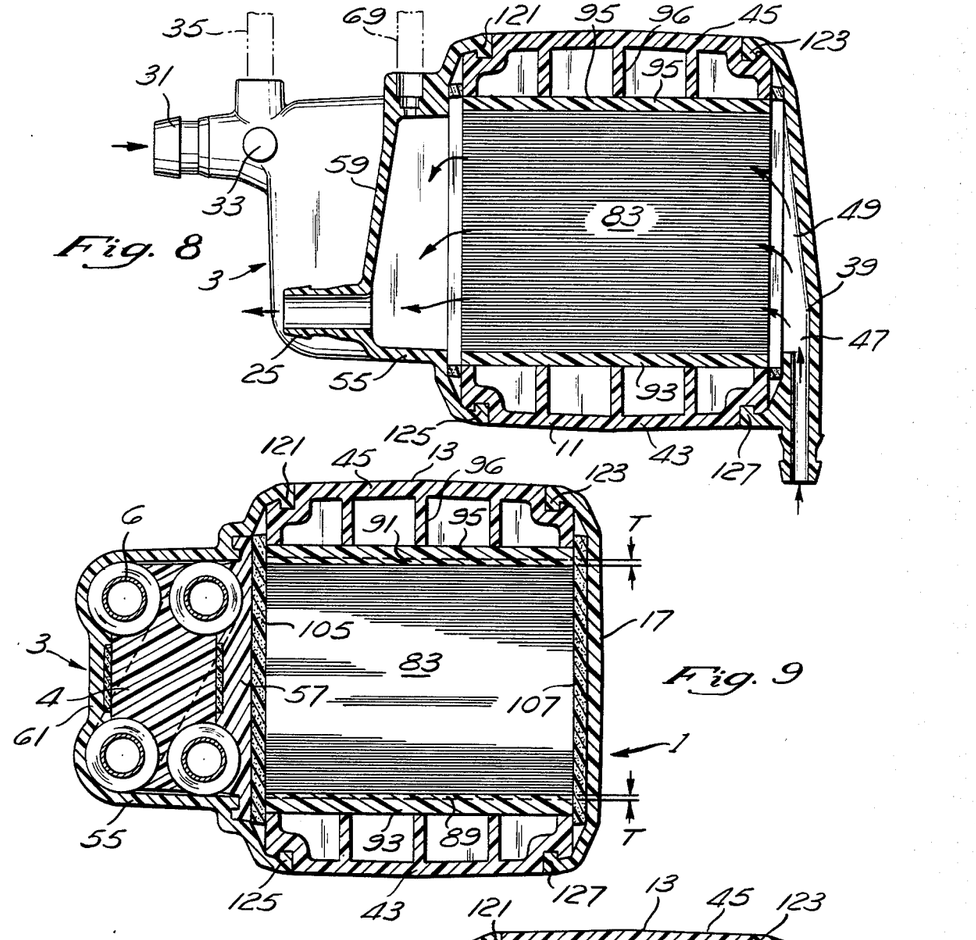
FIGS. 8, 9 and 10 are section views taken along 8—8, 9—9 and 10—10 in FIG. 4; lines
Figure 10:
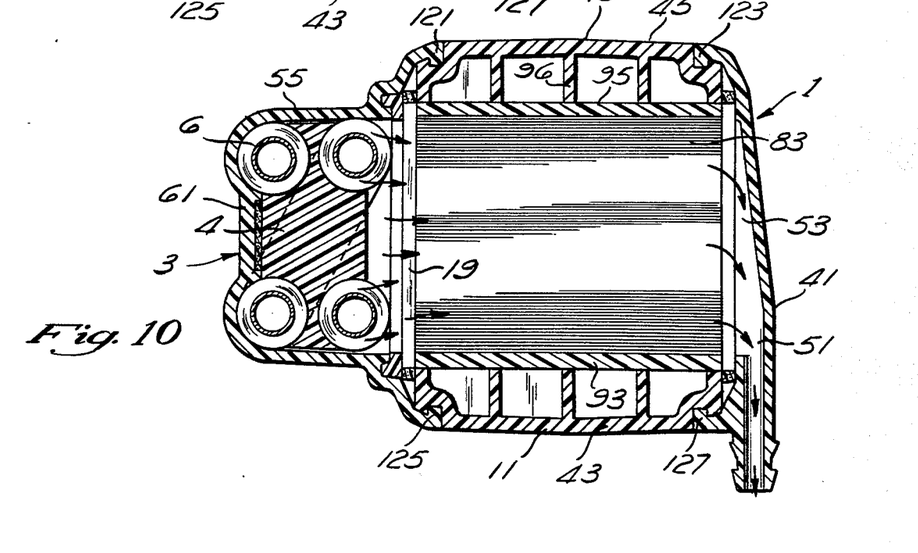

Still another highly advantageous feature of oxygenator 1 is the presence of two substantially identical shims 89 and 91 centrally disposed between the ends of stack 83 and maintained in compression between the top and bottom of stack 83 and side walls 11 and 13 (see FIG. 7). The shims may be discrete elements or integral portions of shim plates such as plates 93 and 95. Each of shims 89 and 91 has at least about the same width as stack 83, a length of from about 10% to about 50% of that of said stack, preferably from about 20% to about 40%, and a thickness (dimension T in FIG. 7) of from about 1% to about 10% of the height of the compacted stack of membrane folds and support screens (i.e. the distance between the top and bottom of the stack) at the ends of the stack, preferably from about 2% to about 5%. Shims 89 and 91 serve to further compress stack 83 in a direction normal to the rectangular membrane folds so as to increase the extent of contact between blood and membrane and further reduce the thickness of the local fluid flow paths, thereby serving to increase the mass transfer rates to and from the blood. However, unlike the shims in prior art oxygenators that extend over a great majority of the length of the overall blood flow paths (see U.S. Pat. Nos. 3,522,885; 3,879,293; 4,219,422 and 4,304,669), the shorter shims 89 and 91 do not give rise to an excessive increase in the blood pressure drop across oxygenator 1. Most preferably, each of shims 89 and 91 has a thickness of about 2% of the height of compacted stack 83 and a length of about one-third of the length of said stack. In the oxygenator shown in the Figures, shim plates 93 and 95 abut a grid of longitudinal and transverse inwardly-extending spacers, e.g. 96 and 98, provided in pressure plates 43 and 45 over the full length and width of said plates to provide stability against buckling of said pressure plates.

The manufacture of oxygenator 1 is quite simple. Blood manifold plate 55, gas manifold plate 37, pressure plates 43 and 45, retainer plate 57 and shim plates 93 and 95 are preferably injection molded parts made of a transparent thermoplastic material such as a polycarbonate. A heat exchanger preassembly may be constructed by fixedly (e.g. adhesively) securing the heat exchanger cooling water coil 6, the coil-supporting core piece 4, blood manifold plate 55 and retainer plate 57 together to form an integral assembly. Membrane 71 may be pleated by folding it about a stack of rectangular folding plates held in a first fixture. The assembly of the membrane and folding plates is then removed and placed in a second fixture, in which the folding plates are replaced one-by-one with the appropriate support screens in the sets 73 and 75 of blood and treating gas pockets. Next, with shim plates 93 and 95 and pressure plates 43 and 45 in position, the resulting assembly of membrane and support screens may be compressed in a hydraulic press to effect the substantial interdigitation of the support screens and form the compacted stack 83. Then, with a thixotropic potting material, e.g. thixotropic polyurethane, applied between manifolds 39 and 41 and between inlet 19 and manifold 59 to the surfaces of gas manifold plate 37, blood manifold plate 55 and retainer plate 57 destined to be closely proximate the folded edges of membrane 71, gas manifold plate 37 and blood manifold plate 55 are fit onto pressure plates 43 and 45. For this purpose, tongues 113, 115, 117, 119, 121, 123, 125 and 127 are provided in plates 37 and 55 which are received within corresponding grooves provided in pressure plates 43 and 45 (plate 55 is also provided with four tongues, not shown in the figures, equivalent to tongues 113, 115, 117 and 119 of plate 37). The compression from the hydraulic press is then released, thereby completing the formation of housing 5 around stack 83. When the thixotropic potting material hardens, it forms shunt blocks 105 and 107. The purpose of these two shunt blocks is to prevent the shunting of blood and treating gas along plates 37 and 57 outside the fold lines of the membrane and thus maintain the integrity of the individual blood and treating gas pockets. Finally, a top seal 109 may be formed by spinning the assembly of oxygenator and heat exchanger in a centrifuge while horizontally oriented with the top wall 7 of the housing 5 facing away from the center of rotation of the centrifuge and a low viscosity potting material, e.g. polyurethane, conducted to the assembly during centrifugation from a rotating dispensing container via a tube connected to the treating gas inlet 23. After hardening of the potting material, the position of the assembly in the centrifuge is reversed and the same procedure followed, with the low viscosity potting material applied through treating gas outlet 21, to form bottom seal 111. The purpose of seals 109 and 111 is to prevent direct contact between the blood and treating gas streams.

In operation, oxygenator 1 of the invention is maintained in a vertical orientation as shown in FIG. 1 with a water input tube 22 connected to inlet 27, a water output tube 24 connected to outlet 29, a treating gas (preferably oxygen or oxygen mixed with air) input tube 26 connected to inlet 23 and a treating gas outlet tube 28 connected to outlet 21. Typically, the principal flow of venous blood from the patient is collected in a venous reservoir 30 along with the output from a cardiotomy reservoir/filter device, a tube 32 carrying the output from the venous reservoir 30 is connected to a blood pump 34, a blood pump output tube 36 is connected to inlet 31, the input treating gas is at essentially atmospheric pressure and an arterialized blood tube 38 leading to an arterial filter is connected to outlet 25. After passing through the arterial filter the arterialized blood is returned to the patient. The assembly of oxygenator 1 and integral heat exchanger 3 is primed, e.g. with sterile saline solution, through inlet 31. Preferably, said assembly is temporarily tilted, so as to tilt inlet 31 by about 30° from horizontal, during the priming step. During a cardiopulmonary bypass operation the patient's blood is cooled in the heat exchanger 3 to a temperature well below the physiological temperature. Subsequently, at the end of the operation, the patient's blood must be rewarmed in the heat exchanger to the physiological temperature. Since the assembly of oxygenator 1 and integral heat exchanger 3 is made of relatively in expensive materials and is of simple construction, it may be disposed after a single use.

A mass transfer device of the present invention may also be used as a blood dialyzer, with a dialysis liquid serving as the treating fluid.

In one specific example of a blood membrane oxygenator 1 of the invention (Example I), 120 Polynetting support screens (60 in blood pockets and 60 in treating gas pockets), each with an overall length of 12 in., an overall width of 3 1/16 in. and a gross surface area of 36 ¾ in.$^2$, are disposed in a compressed stack with 121 Celgard membrane folds. The membrane has a thickness of about 0.002 in. and a nominal pore size of about 0.2 microns. The compressed stack 83 has a volume of 480 cc. and a height at its ends of 2.4 in. The total membrane surface area is 2.4 m.$^2$. Each support screen consists of two fusion-bonded layers of 0.012 in. diameter parallel strands, with the strands of the first layer oriented at about 60° with respect to the strands of the second layer and the individual strands in each layer separated by about 0.06 in. The overall thickness of each screen is about 0.022 in. All the support screens in the oxygenator are cut from the same non-woven open mesh stock material. However, the cutting direction of the longitudinal edges of the blood pocket support screens in the stock material is perpendicular to the cutting direction of the longitudinal edges of the treating gas pocket support screens in the stock material. Additionally, the screens are cut from the stock material so that all strands in the blood pocket support screens are oriented at an angle of about 60° with respect to the fold lines of the membrane and all strands in the treating gas pocket support screens are oriented at an angle of about 30° with respect to the fold lines of the membrane. As shown in FIG. 11, the support screens in the blood pockets are provided with trapezoidal transverse slots adjacent their two opposed ends and the support screens in the treating gas pockets are provided with rectangular transverse slots adjacent their two opposed ends. In this device, each of the two shims 89 and 91 has a thickness of about 2% of the height of compacted stack 83 at the ends of said stack and a length about one-third that of said compacted stack.

In vitro gas transfer and hemodynamic testing has been performed with the particular oxygenator described above as Example I. Oxygen was used as the treating fluid. As the blood flow rate in this device was increased from 2 liters/min. to 6 liters/min., with the ratio of blood volumetric flow rate to oxygen volumetric flow rate held constant at 1:1, the oxygen transfer rate increased linearly from 125 ml./min. to 325 ml./min., the carbon dioxide transfer rate increased linearly from 125 ml./min. to 290 ml./min. and the blood pressure drop across the assembly of oxygenator 1 and integral heat exchanger 3 increased linearly from 60 mm Hg to 180 mm Hg. Minimal hemolysis was observed.

We claim:

1. A mass transfer device for the treatment of blood comprising:
   a housing;
   a pleated, selectively permeable membrane disposed within the housing in substantially rectangular folds defining first and second sets of alternating pockets for the flow of blood and a treating fluid;
   a plurality of discrete non-woven support screens having substantially the same width as said folds, with one of said screens being disposed within each of said pockets of said first and second sets, said membrane and screens being held in said housing as a compacted stack compressed in a direction normal to the substantially rectangular surfaces of said folds with the screens disposed within adjacent blood and treating fluid pockets and separated by the membrane being substantially intedigitated, and with said support screens consisting essentially of a first layer in a first plane of first strands spaced apart and substantially parallel to one another and a second layer in a second plane of second strands apart and substantially parallel to one another, said first layer and said second layer being bonded together at points of contact and said first strands beng oriented with respect to said second strands at an angle of from about 45° to 90°, and said first strands and said second strands in said blood pocket and treating fluid pocket support screens being all oriented at acute angles of from about 20° to about 70 ° with respect to the fold lines of said membrane;
   blood inlet and outlet means in the housing adjacent opposed ends of said stack in communication with the first set of pockets, thereby establishing overall blood flow paths in the first set of pockets along the length of said pockets; and
   treating fluid inlet and outlet means in the housing adjacent opposed ends of said stack in communication with the second set of pockets, thereby establishing overall treating fluid flow paths in the second set of pockets along the length of said pockets.

2. A device of claim 1 wherein said first and second strands in said blood pocket support screens are both of circular cross-section with substantially the same diameter, and said first and second strands in said treating fluid pocket support screens are both of circular cross-section with substantially the same diameter.

3. A device of claim 2 wherein the strand diameter in the blood pocket support screens is substantially the same as the strand diameter in the treating fluid pocket support screens.

4. A device of claim 1 wherein said first and second strands in said blood pocket support screens are both oriented at substantially the same acute angle with respect to said fold lines, and said first and second strands in said treating fluid pocket support screens are both oriented at substantially the same acute angle with respect to said fold lines.

5. A device of claim 4 wherein said first and second strands in said blood pocket support screens are oriented at a larger acute angle with respect to said fold lines than are said first and second strands in said treating fluid pocket support screens.

6. A device of claim 5 wherein said first strands in said blood pocket support screens are oriented with respect to said second strands in said blood pocket support screens at an angle of about 60°, said first strands in said treating fluid pocket support screens are oriented with respect to said second strands in said treating fluid pocket support screens at an angle of about 60°, said first and second strands in said blood pocket support screens are oriented at an angle of about 60° with respect to the fold lines of said membrane, and said first and second strands in said treating fluid pocket support screens are oriented at an angle of about 30° with respect to said fold lines.

7. A device of claim 1 wherein said blood pocket support screens and said treating fluid pocket support screens are both cut from the same non-woven stock material, with the direction of cut in said stock material of the longitudinal edges of said blood pocket support screens being substantially perpendicular to the direction of cut in said stock material of the longitudinal edges of said treating fluid pocket support screens.

8. A device of claim 1 wherein, at least in the vicinity of said blood inlet and outlet means, said blood pocket support screens are slightly wider than said membrane folds.

9. A device of claim 1 wherein said support screens have substantially the same length as said folds, said housing includes two opposed side walls substantially parallel to said folds, and said device includes additionally first and second substantially identical shims, said first shim being in compression between one of said side walls and the top of said compacted stack and said second shim being in compression between the other of said side walls and the bottom of said stack, with each of said shims being centrally disposed between the ends of said stack, having at least about the same width as said stack, having a length of from about 10% to about 50% of that of said stack, and having a thickness of from about 1% to about 10% of the height of said compacted stack at the ends of said stack, whereby said shims serve to substantially improve the mass transfer performance of the device without excessively increasing the blood pressure drop across the device.

10. A device of claim 9 wherein each of said shims has a length of from about 20% to about 40% of the length of said stack.

11. A device of claim 10 wherein each of said shims has a thickness of about 2% of the height of said compacted stack and a length of about one-third of the length of said stack.

12. A mass transfer device for the treatment of blood comprising:

a housing having first and second opposed walls;

a pleated, selectively permeable membrane disposed within the housing as a compressed stack of substantially rectangular folds defining first and second sets of alternating pockets for the flow of blood and a treating fluid, with the fold lines of said membrane being adjacent to said first and second walls;

a plurality of discrete support screens each disposed within one of said pockets of said first and second sets, said screens having substantially the same length and width as said folds;

blood inlet and oulet means in said first wall of the housing adjacent opposed ends of said stack in communication with the first set of pockets, thereby establishing overall blood flow paths in the first set of pockets along the length of said pockets; and treating fluid inlet and outlet means in said second wall of the housing adjacent opposed ends of said stack in communication with the second set of pockets, thereby establishing overall treating fluid flow paths in the second set of pockets along the length of said pockets, with said screens being provided with a pair of transversely-extending cut-out regions adjacent their opposed ends to improve fluid distribution across said pockets, the cut-out regions in the screens disposed in said first set of pockets being tapered with decreasing width away from the blood inlet and blood outlet means and being positioned in a non-overlapping manner with respect to the cut-out regions in the screens disposed in said second set of pockets.

* * * * *